United States Patent [19]

Honig et al.

[11] 4,093,651

[45] June 6, 1978

[54] PRODUCTION OF PERCHLOROMETHYL MERCAPTAN

[75] Inventors: Milton L. Honig, Bronx; Carl C. Greco, Garnersville; Edward N. Walsh, New City, all of N.Y.

[73] Assignee: Stauffer Chemical Company, Westport, Conn.

[21] Appl. No.: 753,119

[22] Filed: Dec. 22, 1976

[51] Int. Cl.$^2$ ............................................. C07C 145/00
[52] U.S. Cl. ................................. 260/543 H; 260/664
[58] Field of Search ..................................... 260/543 H

[56] References Cited

U.S. PATENT DOCUMENTS

| | | | |
|---|---|---|---|
| 2,545,285 | 3/1951 | Kamlet | 260/543 H |
| 2,575,290 | 11/1951 | Ohsol et al. | 260/543 H |
| 2,647,143 | 7/1953 | Pitt et al. | 260/543 H |
| 2,666,081 | 1/1954 | Chirschill | 260/543 H |
| 2,759,969 | 8/1956 | Jonas | 260/543 H |
| 3,014,071 | 12/1961 | Hoyt et al. | 260/543 H |
| 3,673,246 | 6/1972 | Meyer et al. | 260/543 H |
| 3,808,270 | 4/1974 | Rupp et al. | 260/543 H |
| 3,878,243 | 4/1975 | Zupancic | 260/543 H |
| 3,968,155 | 7/1976 | Guerin | 260/543 H |
| 3,993,693 | 11/1976 | Bhutani | 260/543 H |

FOREIGN PATENT DOCUMENTS

| | | | |
|---|---|---|---|
| 508,163 | 12/1954 | Canada | 260/543 H |
| 1,437,908 | 3/1966 | France | 260/543 H |

OTHER PUBLICATIONS

Somovsky, "Chem. Reviews", vol. 58, pp. 509-512 (1958).

Primary Examiner—Norman Morgenstern
Attorney, Agent, or Firm—Roger S. Benjamin

[57] ABSTRACT

A method for improving the yield of perchloromethyl mercaptan by including in the reaction mixture phosphonates or phosphonites, in amounts effective to suppress the formation of undesirable byproducts, such as carbon tetrachloride and sulfur monochloride.

4 Claims, No Drawings

PRODUCTION OF PERCHLOROMETHYL MERCAPTAN

BACKGROUND OF THE INVENTION

This invention relates to improvements in the production of perchloromethyl mercaptan. More particularly, it relates to the use of phosphonates and phosphonites as additives which serve to improve the yield of perchloromethyl mercaptan.

Perchloromethyl mercaptan, $Cl_3CSCl$, also known as trichloromethanesulfenyl chloride has commercial importance as an intermediate in the manufacture of fungicides, bactericides, germicides, herbicides, soil fumigants and pharmaceuticals.

Perchloromethyl mercaptan was first described in a production scheme by Rathke in Annalen, Volume 167, at page 195 (1873). Rathke's method which is still in use today, utilizes an iodine catalyst. The reaction scheme operates most efficiently at temperatures below about 40° C., in accordance with the following equations:

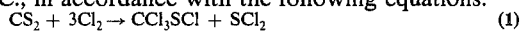

$$CS_2 + 3Cl_2 \rightarrow CCl_3SCl + SCl_2 \qquad (1)$$

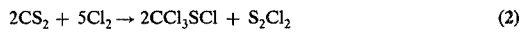

$$2CS_2 + 5Cl_2 \rightarrow 2CCl_3SCl + S_2Cl_2 \qquad (2)$$

$$CS_2 + 3Cl_2 \rightarrow CCl_4 + S_2Cl_2 \qquad (3)$$

In addition to sulfur dichloride, sulfur chloride (also known as sulfur monochloride) and carbon tetrachloride, the reaction can also form thiophosgene and other compounds as unwanted byproducts. Although more volatile byproducts such as carbon tetrachloride and sulfur dichloride can be removed from the reaction mixture by distillation, it is extremely difficult to separate perchloromethyl mercaptan from sulfur chloride by this method. This is due to the fact that the boiling points of perchloromethyl mercaptan and sulfur chloride are very close to each other.

The prior art has proposed several methods for improving the basic Rathke method. For example, U.S. Pat. No. 3,544,625 to Masat, discloses a method for producing perchloromethyl mercaptan by chlorinating carbon disulfide in the presence of a solution of inorganic acids, such as hydrochloric acid. U.S. Pat. No. 3,673,246 to Meyer et al, discloses a continuous process for producing perchloromethyl mercaptan wherein carbon disulfide is reacted with chlorine on or in intimate contact with activated carbon at temperatures of about −5° C. to +100° C. U.S. Pat. No. 3,808,270 to Rupp et al, discloses a continuous process for producing perchloromethyl mercaptan by reacting carbon disulfide and chlorine in a reaction zone filled with granular active carbon completely immersed in the liquid reaction mixture while maintaining temperatures in the range of about 40° C. to about 135° C. U.S. Pat. No. 3,878,243 to Zupancic discloses a homogeneous catalyst system comprising a lead salt of a carboxylic acid which is soluble in carbon disulfide.

Notwithstanding the effectiveness of the above prior art patents as methods for producing perchloromethyl mercaptan (PMM), they do not deal with preventing the tendency of PMM to react with chlorine or sulfur dichloride to form carbon tetrachloride, sulfur, and sulfur monochloride. Mixtures of carbon disulfide, sulfur dichloride and perchloromethyl mercaptan also react in a similar fashion. The reactions which form carbon tetrachloride are believed to be accelerated by trace amounts of metals, such as iron, tin, and bronze, in the reaction mixture.

Small quantities of iron are generally present in the commercial carbon disulfide and chlorine used as reactants for PMM, at levels on the order of parts per million. The chlorine can be treated by passing it through a glass wool filter to remove most of the iron. However, the presence of iron at levels as low as one part per million can be deleterious and capable of effecting significant reductions in the yield of perchloromethyl mercaptan. It has, therefore, been an objective of industry to develop agents capable of ameliorating the effect of metallic impurities present in the reactants and/or catalyst, so that the formation of carbon tetrachloride, sulfur and other undesirable byproducts is suppressed.

Another problem in the production of perchloromethyl mercaptan occurs in the decomposition of sulfur dichloride to sulfur chloride and chlorine in the following manner:

$$2SCl_2 \rightleftharpoons S_2Cl_2 + Cl_2 \qquad (4)$$

This reaction is undesirable due to the fact that the boiling points of perchloromethyl mercaptan and sulfur monochloride are so close to each other that it is impractical to separate them by distillation. Thus, it has also been an objective of industry to develop agents for stabilizing sulfur dichloride to thereby prevent it from forming sulfur monochloride and chlorine.

The present invention has achieved improvements in the production of perchloromethyl mercaptan via the use of small amounts of phosphonates and/or phosphonites as additives which are believed to suppress the formation of the undesirable byproducts occurring in reactions (3) and (4).

DESCRIPTION OF THE PREFERRED EMBODIMENTS

In accordance with the present invention, improved yields of perchloromethyl mercaptan have been achieved by the addition of small amounts of phosphonates and/or phosphonites to the reaction system.

The phosphonates and phosphonites that have been found to be most effective in accomplishing the purposes of the present invention have the following respective structural formulae:

(A)

(B)

In (A), R independently is hydrogen, hydrocarbyl, chlorine, or substituted hydrocarbyl; R' and R" independently are R but not chlorine, however, R, R' and R" cannot all be hydrogen simultaneously. In (B), R independently is hydrogen, hydrocarbyl, chlorine, or substituted hydrocarbyl; R' and R" independently are R but not chlorine or hydrogen.

Typical examples of hydrocarbyl groups are alkyl, cycloalkyl, aralkyl, alkaryl, and aryl, with the alkyl groups having from 1 to about 20 carbon atoms, and preferably from 1 to about 10 carbon atoms. The alkyl groups can be straight, branch chained, or cyclic.

Typical examples of substituted alkyl and substituted aryl as used herein are meant to designate alkyl or aryl groups having attached thereto at least one substituent of the type: halogen, cyano, carboxyl, carboxylate, amido, amino, nitro, hydroxy, or alkoxy, with the proviso that the substituents not adversely affect the preparation of perchloromethyl mercaptan. The preferred substituents are halogen, and most preferably chlorine.

Typical phosphonates and/or phosponites found to be especially effective in increasing the yield of perchloromethyl mercaptan have alkyl and substituted alkyl groups of from about 4 to about 10 carbon atoms.

The addition of the phosphonates and/or phosphonites to the reactants involved in the production of perchloromethyl mercaptan is accomplished most effectively by contacting the additives in situ with carbon disulfide and a catalyst. It is to be noted that the catalyst chosen must be inert to the additives, otherwise the reaction will cease. Thus, for example, the phosphonate and/or phosphonite additives of the present invention will not function with an iodine catalyst.

It has been found that activated carbon as a catalyst is most effective in utilizing the additives of the present invention. The activated carbon catalyst is contacted with the carbon disulfide and chlorine reaction mixture over an extended period of time while maintaining the reaction temperature between about 0° C. and about 135° C.

It should be noted that the reaction temperatures required for batch process production of PMM are generally lower than the temperatures which can be maintained in a continuous process. For example, batch process temperatures generally vary from about 10° C. to about 40° C., when using an activated carbon catalyst. At above about 40° C. in a batch process, PMM might tend to decompose into $CCl_4$ and $S_2Cl_2$. The carbon catalyzed system can operate in a continuous mode at temperatures above 40° C. if done in accordance with U.S. Pat. No. 3,808,270.

The phosphonates and/or phosphonites are generally added in amounts which vary from about 0.01 to about 10%, and preferably from about 0.1 to about 5% by weight of the carbon disulfide feed. Larger amounts can be used, however, no advantage is accrued thereby. In general, it has been found that use of the phosphonates and/or phosphonites in the stated manner significantly reduces the formation of carbon tetrachloride and other unwanted byproducts, and increases the yield of perchloromethyl mercaptan to yields above 95%, based upon the chlorine reacted.

It should be noted that although the phosphonate and/or phosphonite additives are not to be used in catalyst systems which can interract with these additives (i.e. iodine catalyzed system), they can be used to stabilize the crude perchloromethyl mercaptan product, and act to prevent sulfur dichloride from reacting to form sulfur monochloride and chlorine.

In the examples which follow, all parts and percentages are by weight unless otherwise specified.

EXAMPLE 1

(Continuous Reaction)

A 1½ inches I.D. glass tube was filled to a height of 30 inches with 8-12 mesh size granular activated carbon (CXAL coconut charcoal from Union Carbide). The glass reactor was fitted with a top inlet for $CS_2$ feed and a bottom inlet for $Cl_2$ feed as well as a bottom drain for collecting the crude product. A reflux condenser was fitted to the vapor outlet of the column in order to avoid the loss of $CS_2$. $CS_2$ was added to the reactor in an amount just sufficient to cover the catalyst bed. $Cl_2$ was then metered to the reactor until about 90% of the $CS_2$ had been reacted as determined by gas-liquid chromatographic analysis. $Cl_2$ and $CS_2$ were then fed to the reactor simultaneously in the ratio of 3 moles $Cl_2$/mole $CS_2$. Crude PMM was withdrawn from the bottom of the reactor at a rate such that the liquid level in the reactor was maintained at the top of the catalyst bed. The maximum temperature in the reactor was kept at less than or equal to 110° C. by limiting the $CS_2$ feed rate to about 0.16 gm $CS_2$/gm catalyst per hour. The above procedure was then repeated, except that dimethyl methylphosphonate (DMMP) was added to the $CS_2$ feed at a level of 0.5% by weight, based on $CS_2$. The results are tabulated below:

|  | No Additive | 0.5% DMMP |
|---|---|---|
| % $CS_2$ Conversion | 98.0 | 98.8 |
| % Selectivity for PPM | 78.8 | 94.8 |
| % Selectivity for $CCl_4$ | 21.2 | 5.2 |
| % $S_2Cl_2$ in distilled product | 11.0 | 1.9 |
| % PPM yield on $CS_2$ | 77.2 | 93.7 |
| % $CCl_4$ yield on $CS_2$ | 20.8 | 5.1 |

EXAMPLES 2-6

Batch Reaction 76 grams of carbon disulfide (1 mole), 30 grams of activated carbon (CXAL coconut charcoal from Union Carbide) and 0.28 grams of dimethyl ethyl phosphonoacetate were placed into a 250 ml. glass jacketed flask fitted with a chlorine inlet tube, dry ice condenser and mechanical stirrer. Thermostated water at a temperature of 35° C. was continuously cycled through the jacket. The solution was stirred and 182.9 grams of chlorine were bubbled through the solution over a 4 hour period. A total of 247 grams of liquid residue was recovered from the jacketed flask after separation from the charcoal. This material was analyzed by gasliquid chromatography(glc.). The results are shown in the Table below. The procedure was again successively repeated with different additives and with no additive, with the results shown in the Table.

TABLE

| Example | Additive | PPM Yield, %[1] | % $CCl_4$ |
|---|---|---|---|
| 2 | Dimethyl ethyl phosphonoacetate $(CH_3O)_2PCH_2COOC_2H_5$ $\parallel$ $O$ | 85 | 1 |
| 3 | Dimethyl methylphosphonate[2] $(CH_3O)_2PCH_3$ $\parallel$ $O$ | 100 | 0 |
| 4 | Tetra($\beta$-chloroethyl) ethylene bisphosphonate $[(ClCH_2CH_2O)_2PCH_2]_2$ $\parallel$ $O$ | 99.8 | 0.2 |
| 5 | Tetraethyl methylene bisphosphonate $[(CH_3CH_2O)_2P]_2CH_2$ $\parallel$ $O$ | 99.8 | 0.2 |
| 6 | None | 77 | 21 |

[1] All yields based upon $Cl_2$ consumed, analysis by glc.
[2] Charcoal was washed with HCl, then neutralized.

What is claimed is:

1. In a method for producing perchloromethyl mercaptan via the catalytic reaction of chlorine and carbon disulfide, the improvement which comprises:

(1) contacting the reactants with additive selected from the group consisting of phosphonates, phosphonites, or blends thereof, where said phosphonates are represented by the formula:

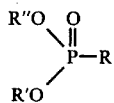

wherein R independently is hydrogen, hydrocarbyl, chlorine, or substituted hydrocarbyl; R' and R" independently are R but not chlorine; however, R, R', and R" cannot all be hydrogen simultaneously; and where said phosphonites are represented by the formula:

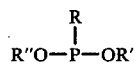

wherein R independently is hydrogen, hydrocarbyl, chlorine, or substituted hydrocarbyl; R' and R" independently are R but not chlorine or hydrogen; said additives being added to the reaction system in amounts which vary in the range of from about 0.01 to about 10% by weight of the carbon disulfide feed, and (2) using an activated carbon catalyst inert to said additive.

2. In a method for producing perchloromethyl mercaptan via the catalytic reaction of chlorine and carbon disulfide, the improvement which comprises:

(1) contacting the reactants with additive selected from the group consisting of dimethyl methylphosphonate, dimethyl ethyl phosphonoacetate, tetra(beta-chloroethyl) ethylene bisphosphonate, tetraethyl methylene bisphosphonate, or blends thereof, said additives being added to the reaction system in amounts which vary in the range of from about 0.01 to about 10% by weight of the carbon disulfide feed, and (2) using an activated carbon catalyst inert to said additive.

3. The method of claim 1 wherein said phosphonates and/or phosphonites are alkyl and contain from about 1 to about 10 carbon atoms.

4. The method of claim 1 wherein said phosphonates and/or phosphonites vary from about 0.1 to about 5% by weight of the carbon disulfide feed.

* * * * *

UNITED STATES PATENT AND TRADEMARK OFFICE
CERTIFICATE OF CORRECTION

PATENT NO. : 4,093,651

DATED : June 6, 1978

INVENTOR(S) : Milton L. Honig et al.

It is certified that error appears in the above-identified patent and that said Letters Patent are hereby corrected as shown below:

Column 4, Line 19, delete "PPM" and add -- PMM --;

Column 4, Line 22, delete "PPM" and add -- PMM --;

Column 4, Line 46, delete "PPM" and add -- PMM --.

Signed and Sealed this

Fifteenth Day of May 1979

[SEAL]

Attest:

RUTH C. MASON
Attesting Officer

DONALD W. BANNER
Commissioner of Patents and Trademarks